United States Patent
Yan

(10) Patent No.: US 12,357,618 B2
(45) Date of Patent: Jul. 15, 2025

(54) RAPAMYCIN (RAPA) SELF-MICROEMULSIFYING INJECTION AND PREPARATION METHOD AND USE THEREOF

(71) Applicant: Pengke Yan, Guangzhou (CN)

(72) Inventor: Pengke Yan, Guangzhou (CN)

( * ) Notice: Subject to any disclaimer, the term of this patent is extended or adjusted under 35 U.S.C. 154(b) by 0 days.

(21) Appl. No.: 18/098,654

(22) Filed: Jan. 18, 2023

(65) Prior Publication Data

US 2023/0241040 A1    Aug. 3, 2023

(30) Foreign Application Priority Data

Jan. 28, 2022  (CN) .......................... 202210106827.5

(51) Int. Cl.
| | | |
|---|---|---|
| A61K 31/436 | (2006.01) | |
| A61K 9/00 | (2006.01) | |
| A61K 9/107 | (2006.01) | |
| A61K 47/10 | (2017.01) | |
| A61K 47/12 | (2006.01) | |
| A61K 47/14 | (2017.01) | |
| A61K 47/20 | (2006.01) | |
| A61K 47/22 | (2006.01) | |

(52) U.S. Cl.
CPC .......... *A61K 31/436* (2013.01); *A61K 9/0019* (2013.01); *A61K 9/1075* (2013.01); *A61K 47/10* (2013.01); *A61K 47/12* (2013.01); *A61K 47/14* (2013.01); *A61K 47/20* (2013.01); *A61K 47/22* (2013.01)

(58) Field of Classification Search
CPC .. A61K 31/436; A61K 9/0019; A61K 9/1075; A61K 47/10; A61K 47/12; A61K 47/14; A61K 47/20; A61K 47/22; A61P 35/00; A61P 37/06
See application file for complete search history.

(56) References Cited

U.S. PATENT DOCUMENTS

2004/0006012 A1 * 1/2004 Cottens ................ A61K 31/19
                                                                    514/183
2009/0074786 A1    3/2009 Dor et al.

FOREIGN PATENT DOCUMENTS

| CN | 102008437 B | 11/2012 |
|---|---|---|
| EP | 0041795 B1 * | 1/1985 |
| EP | 0649659 A1 | 4/1995 |

OTHER PUBLICATIONS

"Polyethylene Glycol Monostearate", Chemical Book, Mar. 12, 2010. Retrieved from: https://web.archive.org/web/20100312235629/ https://www.chemicalbook.com/ChemicalProductProperty_EN_CB6404723.htm (Year: 2010).*

(Continued)

*Primary Examiner* — Marianne C Seidel
*Assistant Examiner* — Joshua A Atkinson
(74) *Attorney, Agent, or Firm* — Muncy, Geissler, Olds & Lowe, P.C.

(57) ABSTRACT

A rapamycin (RAPA) self-microemulsifying injection includes a drug stock solution and a diluent. The drug stock solution includes a drug solvent, an antioxidant, and RAPA, and the diluent includes a surfactant and water. RAPA is dissolved in the drug solvent. After the stock solution is diluted with the diluent, the solution is self-assembled into a microemulsion under the action of a surfactant, and RAPA is encapsulated in the microemulsion, which improves the solubility and stability of RAPA.

7 Claims, 4 Drawing Sheets

(56) References Cited

OTHER PUBLICATIONS

Millapore Sigma, "Propylene glycol", retrieved 2024 from: https://www.sigmaaldrich.com/US/en/product/aldrich/w294004 (Year: 2024).*

Millapore Sigma, "Ethyl alcohol, pure", retrieved 2024 from: https://www.sigmaaldrich.com/US/en/product/sial/32205m?srsltid=AfmBOoqUD0N2AOWiExFxwv3LMGOnf2BUrjrqrt_zU6zDnkLo-3_I_GWT (Year: 2024).*

Kim et al, "Enhanced bioavailability of sirolimus via preparation of solid dispersion nanoparticles using a supercritical antisolvent process", Int Jour Nano, 2011, 6, pp. 2997-3009. (Year: 2011).*

* cited by examiner

RAPAMYCIN (RAPA) SELF-MICROEMULSIFYING INJECTION AND PREPARATION METHOD AND USE THEREOF

CROSS REFERENCE TO THE RELATED APPLICATIONS

This application is based upon and claims priority to Chinese Application No. 202210106827.5, filed on Jan. 28, 2022, the entire contents of which are incorporated herein by reference.

TECHNICAL FIELD

The present disclosure specifically relates to a rapamycin (RAPA) self-microemulsifying injection and a preparation method and use thereof.

BACKGROUND

RAPA (molecular weight: 914.2), also known as sirolimus, is a macrolide compound with immunosuppressive activity and is used as an inhibitor for transplant rejection in organ transplant patients. Moreover, it has been reported that RAPA can not only serve as an immunosuppressant but also induce cancer cell death and destroy cancer cells. It has been confirmed that RAPA has antitumor activity. RAPA exhibits high antitumor activity in vitro, but RAPA when orally administered in vivo exhibits unsatisfactory antitumor activity, which may be related to the low water solubility and low bioavailability of RAPA. Thus, there are a large number of studies on new dosage forms for RAPA. However, due to the poor stability and low water solubility of RAPA, how to improve the stability of RAPA in a dosage form and how to increase the concentration of RAPA in a dosage form are challenges in the preparation of RAPA dosage forms. The latest reports have shown that albumin nanoparticles (nab-sirolimus) developed by Abramis BioScience Inc. and EOC PHARMA are mainly used in the treatment of advanced (metastatic or locally advanced) malignant perivascular epithelioid cell (PEC) tumors but have problems such as complicated preparation process, high preparation cost, and large inter-batch difference, which still does not overcome the poor stability and low solubility of RAPA in a formulation.

CN102008437B discloses an ophthalmic RAPA microemulsifying injection and a preparation method thereof, where the highest concentration of RAPA in the RAPA microemulsifying injection can reach 20 g/1,000 mL. The ophthalmic RAPA microemulsifying injection in this technical solution has a low cost, and the stability and solubility of RAPA in the microemulsifying injection have been greatly improved compared with the formulations in the prior art. However, the solubility of RAPA still cannot meet the requirements of existing clinical medication and can still be further improved, and the stability of RAPA also needs to be further improved.

Given this, the present disclosure provides a RAPA self-microemulsifying injection in which RAPA has high solubility and high stability.

SUMMARY

A first objective of the present disclosure is to provide a RAPA self-microemulsifying injection, which solves the technical problem that the existing RAPA injections have low solubility and poor stability.

A second objective of the present disclosure is to provide a preparation method of the RAPA self-microemulsifying injection.

A third objective of the present disclosure is to provide a use of the RAPA self-microemulsifying injection in the treatment of a cancer.

The objectives of the present disclosure are achieved by the following technical solutions.

A RAPA self-microemulsifying injection is provided, including a drug stock solution and a diluent, where the drug stock solution includes a drug solvent, an antioxidant, and RAPA, and the diluent includes a surfactant and water.

In the RAPA self-microemulsifying injection of the present disclosure, after the stock solution is diluted with the diluent, the solution is self-assembled into a microemulsion under the action of the surfactant, and the RAPA is encapsulated in the microemulsion, which improves the solubility of RAPA.

In the present disclosure, in the drug stock solution, a mass-to-volume ratio of the RAPA to the drug solvent is 0.1 to 60 mg/mL, and a mass-to-volume ratio of the antioxidant to the drug solvent is 0.0001 to 0.05 mg/mL.

In the RAPA self-microemulsifying injection of the present disclosure, the drug solvent includes absolute ethanol and a latent solvent, and the latent solvent is one or more selected from the group consisting of propylene glycol (PG), polyethylene glycol (PEG) 300, and PEG 400. The drug solvent of the present disclosure is a mixed solvent of two or more solvents in different proportions to dissolve RAPA, which can greatly improve the solubility of RAPA.

Further, the drug solvent includes absolute ethanol with a volume percentage of 1% to 50% and a latent solvent with a volume percentage of 50% to 99%.

In the present disclosure, the antioxidant is one or more selected from the group consisting of 2,6-tert-butyl-4-methylphenol, bis(3,5-tert-butyl-4-hydroxyphenyl)sulfide, tetrakis[β-(3,5-tert-butyl-4-hydroxyphenyl)propionic acid], pentaerythritol oleate, butylated hydroxytoluene (BHT), α-tocopherol, thioglycerin, and butylated hydroxyanisole (BHA).

The present disclosure may be improved as follows: The drug stock solution further includes an antioxidant synergist, and the antioxidant synergist is anhydrous citric acid.

Further, the mass-to-volume ratio of the antioxidant synergist to the drug solvent is 0.00025 to 0.025 mg/mL.

In the RAPA self-microemulsifying injection of the present disclosure, the surfactant is an amphiphilic surfactant.

Further, the surfactant is a PEG stearate. The present disclosure uses a PEG stearate amphiphilic surfactant. Compared with Tween-80 and polyoxyethylene castor oil surfactants, the PEG stearate amphiphilic surfactant has the following advantages: (1) The PEG stearate amphiphilic surfactant can form a spheroidal micelle in an aqueous solution. Because the PEG stearate amphiphilic surfactant has a long hydrophobic hydrocarbon chain, a large micellar nucleus can be formed, which can be loaded with large amounts of RAPA. (2) The PEG stearate amphiphilic surfactant has a lower critical micelle concentration (CMC) than other surfactants and thus is easier to form a desired nanoemulsion than other surfactants. (3) The PEG stearate amphiphilic surfactant can reduce histamine reactions and thus can reduce allergic reactions after injection, resulting in high safety.

The present disclosure may be improved as follows: the diluent further includes a metal chelating agent.

Further, the metal chelating agent is one or more selected from the group consisting of ethylenediamine tetraacetic acid (EDTA), nitrilotriacetic acid (NTA), diethylenetriaminepentaacetic acid (DTPA) and a salt thereof, citric acid, tartaric acid, gluconic acid, hydroxyethylethylenediaminetriacetic acid (HEDTA), polyacrylic acid (PAA), polymethylacrylic acid (PMAA), hydrolyzed polymaleic anhydride (HPMA), fumaric acid (transbutenedioic acid)-propenesulfonic acid copolymer, dihydroxyethylglycine, and calcium disodium edetate.

In some embodiments of the present disclosure, the diluent includes a surfactant with a volume percentage of 0.5% to 50%, absolute ethanol with a volume percentage of 0.5% to 10%, and water with a volume percentage of 40% to 99%.

Further, a mass-to-volume ratio of the metal chelating agent to the diluent is 0.1 to 10 mg/mL.

A preparation method of the RAPA self-microemulsifying injection is provided, including the following steps:

(1) thoroughly mixing the drug solvent and the antioxidant to obtain a mixed solution, adding the RAPA to the mixed solution, and then adding the antioxidant and the antioxidant synergist to obtain the drug stock solution;

(2) thoroughly mixing the surfactant, the water, and the metal chelating agent to obtain the diluent; and (3) diluting the drug stock solution with the diluent to a desired concentration to obtain the RAPA self-microemulsifying injection for use.

The use of the RAPA self-microemulsifying injection in the treatment of a cancer is provided.

Further, the use of the RAPA self-microemulsifying injection in the treatment of large intestine cancer and kidney cancer is provided.

Compared with the prior art, the RAPA self-microemulsifying injection of the present disclosure has the following beneficial effects:

(1) The RAPA self-microemulsifying injection of the present disclosure includes a drug stock solution and a diluent, where RAPA is dissolved in a drug solvent. After the drug stock solution is diluted with the diluent, the solution is self-assembled into a microemulsion under the action of a surfactant, and RAPA is encapsulated in the microemulsion, which improves the solubility and stability of RAPA.

(2) The drug solvent in the drug stock solution of the present disclosure includes two or more drug solvents and can significantly improve the solubility of RAPA in the solvent, which can be as high as 60 mg/mL; a PEG stearate amphiphilic surfactant is used for the spontaneous formation of a microemulsifying solution, which further improves the solubility, safety, and stability of RAPA.

(3) In the RAPA self-microemulsifying injection of the present disclosure, an antioxidant, a metal chelating agent, and an antioxidant synergist are added, which solves the problem that RAPA is easily oxidized and hydrolyzed in a solution and greatly improves the stability of RAPA; RAPA can be diluted with an isotonic solution for injection to any desired concentration to obtain a high-concentration RAPA self-microemulsifying injection that can be injected intravenously.

DETAILED DESCRIPTION OF THE EMBODIMENTS

Figure 1:
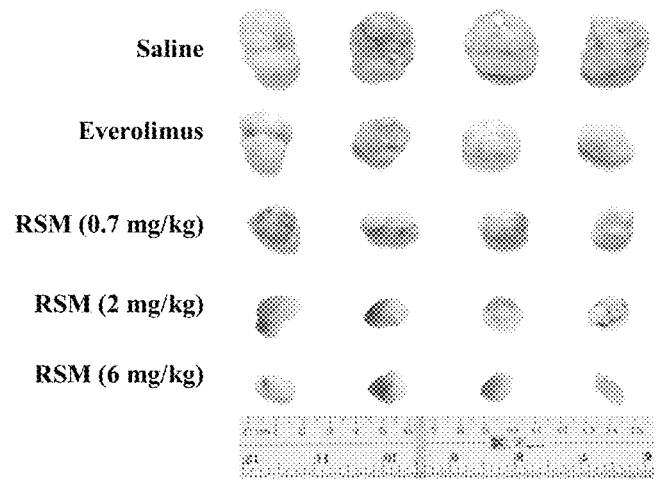
FIGS. 1-3 show the treatment results of the RAPA self-microemulsifying injection in Example 1 for large intestine cancer.

The present disclosure is further described below in conjunction with specific examples, such that those skilled in the art can understand and implement the technical solutions of the present disclosure. In the examples, an amount of the antioxidant added is measured by a mass-to-volume ratio of the antioxidant to the drug solvent (unit: mg/mL); an amount of the antioxidant synergist added is measured by a mass-to-volume ratio of the antioxidant synergist to the drug solvent (unit: mg/mL); and an amount of the metal chelating agent added is measured by a mass-to-volume ratio of the metal chelating agent to the diluent (unit: mg/mL).

Example 1

A RAPA self-microemulsifying injection was provided, including a drug stock solution and a diluent, where the drug stock solution and the diluent respectively included the following components:

| a. drug stock solution | |
|---|---|
| RAPA | 20 mg |
| absolute ethanol | 0.5 mL |
| PEG 400 | 0.5 mL |
| BHT | 0.5 µg |
| anhydrous citric acid | 2.5 µg |

| b. diluent | |
|---|---|
| PEG-15 hydroxystearate | 0.8 mL |
| absolute ethanol | 0.2 mL |
| water for injection (WFI) | 1.0 mL |
| calcium disodium edetate | 0.008 g |

The RAPA self-microemulsifying injection was specifically prepared through the following steps:

(1) 0.5 mL of absolute ethanol and 0.5 mL of a PEG 400 solution were thoroughly mixed to obtain a mixed solution, and RAPA was added to the mixed solution. 0.5 µg of the antioxidant and 2.5 µg of anhydrous citric acid were added to obtain a 20 mg/mL drug stock solution.

(2) 0.8 mL of PEG-15 hydroxystearate, 0.2 mL of absolute ethanol, and 1.0 mL of WFI were taken and thoroughly mixed. 0.008 g of the metal chelating agent was added, and the resulting mixture was thoroughly mixed to obtain the diluent.

(3) The drug stock solution and the diluent each were filtered, sterilized, and stored in a sealed manner at 4° C. For use, the drug stock solution was diluted with the diluent to a desired concentration to obtain the RAPA self-microemulsifying injection.

Example 2

A RAPA self-microemulsifying injection was provided, including a drug stock solution and a diluent, where the drug stock solution and the diluent respectively included the following components:

| a. drug stock solution | |
|---|---|
| RAPA | 20 mg |
| absolute ethanol | 0.5 mL |
| PEG 300 | 0.5 mL |
| α-tocopherol | 0.5 µg |
| anhydrous citric acid | 2.5 µg |

| b. diluent | |
|---|---|
| PEG-10 hydroxystearate | 0.8 mL |
| absolute ethanol | 0.2 mL |
| WFI | 1.0 mL |
| EDTA | 0.004 g |

The RAPA self-microemulsifying injection was specifically prepared through the following steps:

(1) 0.5 mL of absolute ethanol and 0.5 mL of a PEG 300 solution were thoroughly mixed to obtain a mixed solution, and RAPA was added to the mixed solution. 0.5 µg of the antioxidant and 2.5 µg of anhydrous citric acid were added to obtain a 20 mg/mL drug stock solution.

(2) 0.8 mL of PEG-10 hydroxystearate, 0.2 mL of absolute ethanol, and 1.0 mL of WFI were taken and thoroughly mixed. 0.004 g of the metal chelating agent was added, and the resulting mixture was thoroughly mixed to obtain the diluent.

(3) The drug stock solution and the diluent each were filtered, sterilized, and then stored in a sealed manner at 4° C. For use, the drug stock solution was diluted with the diluent to a desired concentration to obtain the RAPA self-microemulsifying injection.

Example 3

A RAPA self-microemulsifying injection was provided, including a drug stock solution and a diluent, where the drug stock solution and the diluent respectively included the following components:

| a. drug stock solution | |
|---|---|
| RAPA | 10 mg |
| absolute ethanol | 0.4 mL |
| PEG 400 | 0.6 mL |
| thioglycerin | 0.1 µg |
| anhydrous citric acid | 5 µg |

| b. diluent | |
|---|---|
| PEG-15 hydroxystearate | 0.8 mL |
| absolute ethanol | 0.2 mL |
| WFI | 1.0 mL |
| EDTA | 0.005 g |

The RAPA self-microemulsifying injection was specifically prepared through the following steps:

(1) 0.5 mL of absolute ethanol and 0.5 mL of a PEG 400 solution were thoroughly mixed to obtain a mixed solution, and RAPA was added to the mixed solution. 0.1 µg of the antioxidant and 5 µg of anhydrous citric acid were added to obtain a 10 mg/mL drug stock solution.

(2) 0.8 mL of PEG-15 hydroxystearate, 0.2 mL of absolute ethanol, and 1.0 mL of WFI were taken and thoroughly mixed. 0.005 g of the metal chelating agent was added, and the resulting mixture was thoroughly mixed to obtain the diluent.

(3) The drug stock solution and the diluent each were filtered, sterilized, and then stored in a sealed manner at 4° C. For use, the drug stock solution was diluted with the diluent to a desired concentration to obtain the RAPA self-microemulsifying injection.

Example 4

A RAPA self-microemulsifying injection was provided, including a drug stock solution and a diluent, where the drug stock solution and the diluent respectively included the following components:

| a. drug stock solution | |
|---|---|
| RAPA | 5 mg |
| absolute ethanol | 0.5 mL |
| PEG 400 | 0.5 mL |
| thioglycerin | 0.5 µg |
| anhydrous citric acid | 2.5 µg |

| b. diluent | |
|---|---|
| PEG-15 hydroxystearate | 0.8 mL |
| absolute ethanol | 0.2 mL |
| WFI | 1.0 mL |
| calcium disodium edetate | 0.008 g |

The RAPA self-microemulsifying injection was specifically prepared through the following steps:

(1) 0.5 mL of absolute ethanol and 0.5 mL of a PEG 400 solution were thoroughly mixed to obtain a mixed solution, RAPA was added to the mixed solution, and then 0.5 µg of the antioxidant and 2.5 µg of anhydrous citric acid were added to obtain a 5 mg/mL drug stock solution.

(2) 0.8 mL of PEG-15 hydroxystearate, 0.2 mL of absolute ethanol, and 1.0 mL of WFI were taken and thoroughly mixed. 0.008 g of the metal chelating agent was added, and the resulting mixture was thoroughly mixed to obtain the diluent.

(3) The drug stock solution and the diluent each were filtered, sterilized, and then stored in a sealed manner at 4° C. For use, the drug stock solution was diluted with the diluent to a desired concentration to obtain the RAPA self-microemulsifying injection.

Example 5

A RAPA self-microemulsifying injection was provided, including a drug stock solution and a diluent, where the drug stock solution and the diluent respectively included the following components:

| a. drug stock solution | |
|---|---|
| RAPA | 60 mg |
| absolute ethanol | 0.5 mL |
| PEG 400 | 0.5 mL |
| BHT | 0.5 µg |
| anhydrous citric acid | 2.5 µg |

| b. diluent | |
|---|---|
| PEG-15 hydroxystearate | 0.8 mL |
| absolute ethanol | 0.2 mL |
| WFI | 1.0 mL |
| calcium disodium edetate | 0.008 g |

The RAPA self-microemulsifying injection was specifically prepared through the following steps:

(1) 0.5 mL of absolute ethanol and 0.5 mL of a PEG 400 solution were thoroughly mixed to obtain a mixed solution, RAPA was added to the mixed solution. 0.5 μg of the antioxidant and 2.5 μg of anhydrous citric acid were added to obtain a 60 mg/mL drug stock solution.

(2) 0.8 mL of PEG-15 hydroxystearate, 0.2 mL of absolute ethanol, and 1.0 mL of WFI were taken and thoroughly mixed. 0.008 g of the metal chelating agent was added, and the resulting mixture was thoroughly mixed to obtain the diluent.

(3) The drug stock solution and the diluent each were filtered, sterilized, and then stored in a sealed manner at 4° C. For use, the drug stock solution was diluted with the diluent to a desired concentration to obtain the RAPA self-microemulsifying injection.

Example 6

Verification of the Stability of a RAPA Self-Microemulsifying Injection

The stock solution and the diluent prepared in Example 3 were mixed in a volume ratio of 1:2. The resulting mixture was diluted with each of normal saline (NS) and 5% glucose injection according to a volume ratio of 1:10 and placed at room temperature for 0 h, 2 h, 4 h, 5 h, 6 h, 8 h, 10 h, 12 h, and 24 h. The RAPA content and isomer content were detected by high-performance liquid chromatography (HPLC) to observe the stability of RAPA in the self-microemulsifying injection within 24 h. Results are shown in Table 1 and Table 2. When the RAPA self-microemulsifying injection prepared in Example 3 was diluted with NS or 5% glucose injection and then placed at room temperature, a drug concentration was maintained at 90% or higher within 12 h, which met clinical needs.

TABLE 1

Changes in RAPA content within 12 h after dilution with NS

| Time point | Drug content |
|---|---|
| 20-08-0 h | 101.56% |
| 20-08-2 h | 98.96% |
| 20-08-4 h | 98.66% |
| 20-08-6 h | 99.28% |
| 20-08-8 h | 96.61% |
| 20-08-10 h | 93.87% |
| 10-08-12 h | 90.84% |

TABLE 2

Changes in RAPA content within 12 h after dilution with 5% glucose injection

| Time point | Drug content |
|---|---|
| 20-08-0 h | 101.63% |
| 20-08-2 h | 100.58% |
| 20-08-4 h | 101.38% |
| 20-08-6 h | 98.66% |
| 20-08-8 h | 99.28% |
| 20-08-10 h | 95.47% |
| 10-08-12 h | 92.54% |

Example 7

The therapeutic effect of RAPA self-assembled microemulsion for large intestine cancer in vivo Modeling of HCT116 solid tumor-bearing mice: 20 female BALB/c nude mice each with a body weight of 20 g were selected, and each was subcutaneously inoculated with 0.2 mL of the prepared HCT116 cell suspension including $5\times10^6$ cells.

Grouping and administration: After the inoculation, the mice were randomly divided into five groups, including RAPA self-assembled microemulsion groups: 0.7 mg/kg, 2 mg/kg, and 6 mg/kg, namely, low-dose group, medium-dose group, and high-dose group; a 5 mg/kg everolimus control group; and an NS control group, where there were 6 mice in each group.

Figure 2:
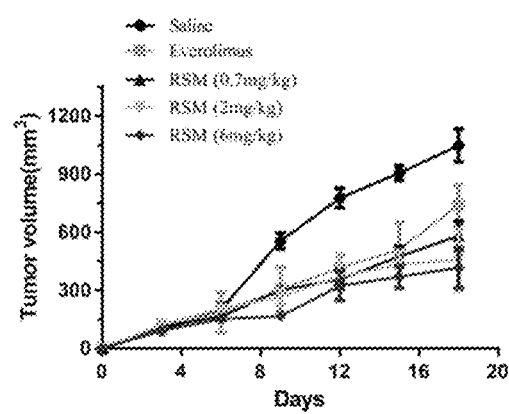
Figure 3:
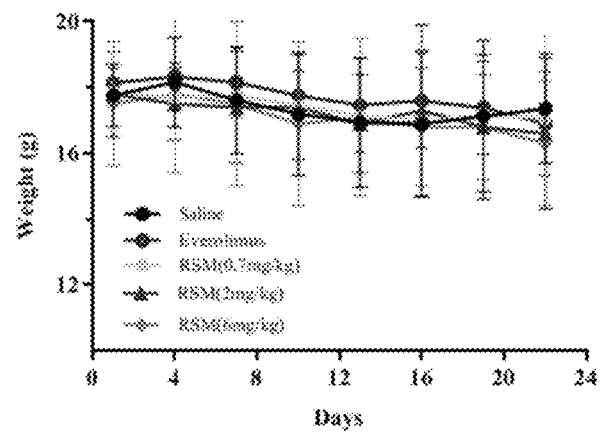
Figure 4:
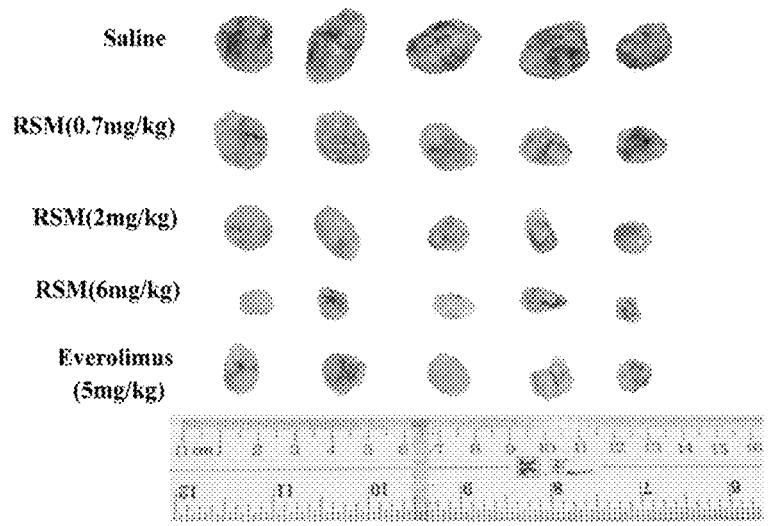
FIGS. 4-7 show the treatment results of the RAPA self-microemulsifying injection in Example 2 for kidney cancer.
Figure 5:
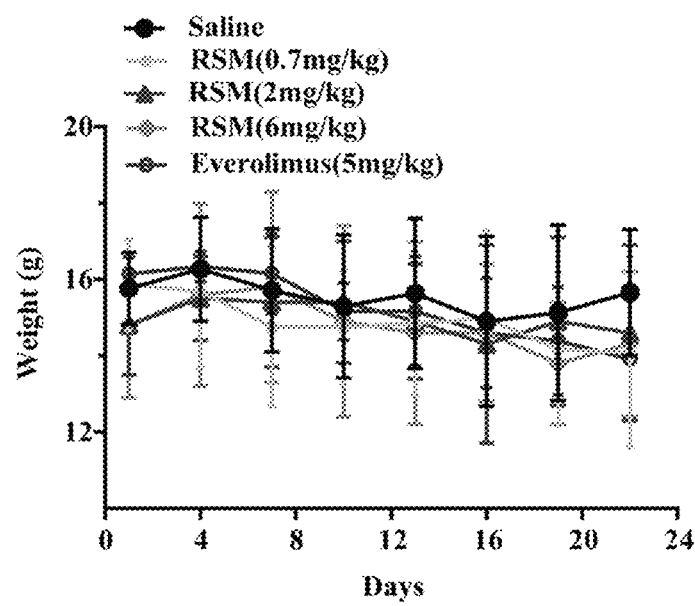
Figure 6:
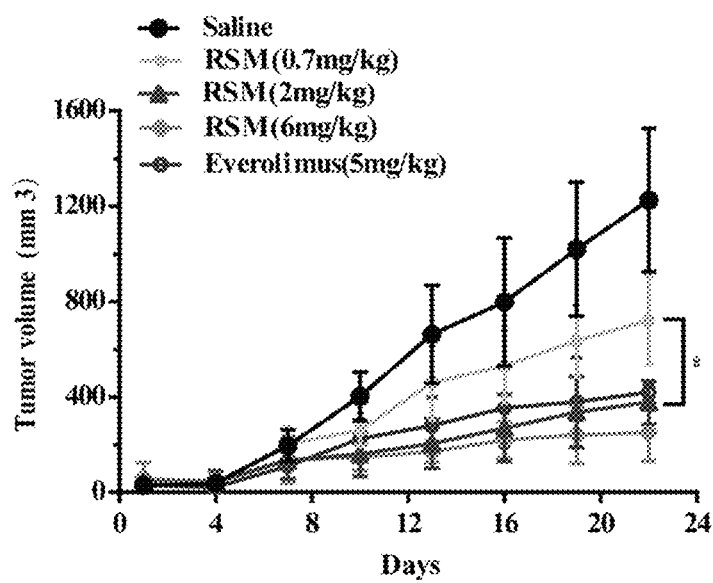
Figure 7:
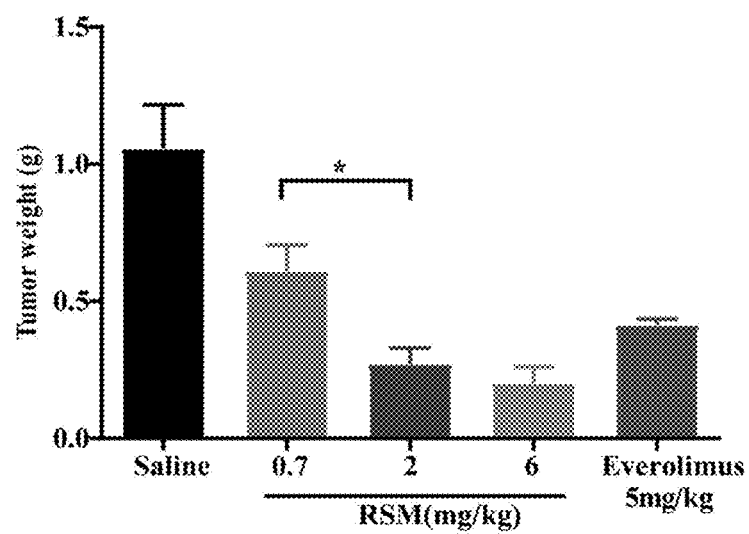

The stock solution of Example 1 was diluted with the diluent to a concentration of 5 mg/mL and then diluted with NS for injection to a desired concentration of 0.35 mg/mL. On day 5 after inoculation, each mouse was injected with 0.2 mL of a diluted solution through the tail vein once every two days (about 56 h), where the administration was conducted consecutively for 21 d. After administration, the tumor volume was measured every other day and each of the mice was weighed. 50 h after the last administration, each of the mice was weighed, blood was collected, the mice were sacrificed, and tumors were collected, weighed, and measured for tumor size. Results are shown in FIG. 1 to FIG. 3, and the results showed that, compared with the NS group and the everolimus control group, in the RAPA self-microemulsion administration groups, the tumor volume was significantly reduced and was positively correlated with an administered RAPA concentration.

Example 8

The therapeutic effect of RAPA self-assembled microemulsion for kidney cancer in vivo Modeling of 769-p solid tumor-bearing mice: 20 female BALB/c nude mice each with a body weight of 20 g were selected, and each was subcutaneously inoculated with 0.2 mL of the prepared 769-p cell suspension including $5\times10^6$ cells.

Grouping and administration: After the inoculation, the mice were randomly divided into five groups, including RAPA self-assembled microemulsion groups: 0.7 mg/kg, 2 mg/kg, and 6 mg/kg, namely, low-dose group, medium-dose group, and high-dose group; a 5 mg/kg everolimus control group; and an NS control group, where there were 6 mice in each group.

The stock solution of Example 2 was diluted with the special diluent to a concentration of 5 mg/mL and then diluted with NS for injection to a desired concentration of 0.35 mg/mL. On day 5 after inoculation, each mouse was injected with 0.2 mL of a diluted solution through the tail vein once every two days (about 56 h), where the administration was conducted consecutively for 21 d. After administration, the tumor volume was measured every other day and each of the mice was weighed. 50 h after the last administration, each of the mice was weighed, blood was collected, the mice were sacrificed, and tumors were collected, weighed, and measured for tumor size. Results are shown in FIG. 4 to FIG. 7, and the results showed that, compared with the NS group and the everolimus control group, in the RAPA self-microemulsion administration groups, the tumor volume was significantly reduced, where a tumor volume in the high-concentration group was reduced by 60% or more.

The different implementations of the present disclosure are described in detail through the above examples, but the implementations of the present disclosure are not limited thereto. Those of ordinary skill in the art can realize the objective of the present disclosure according to the disclosure of the present disclosure. Any improvement and deformation made based on the concept of the present disclosure should fall within the protection scope of the present disclosure, and the specific protection scope should be subject to the protection scope defined by the claims.

What is claimed is:

1. A rapamycin (RAPA) self-microemulsifying injection, comprising:
   a drug stock solution; and
   a diluent,
   wherein the drug stock solution comprises a drug solvent, an antioxidant, and RAPA, and the diluent comprises a surfactant and water; the drug stock solution further comprises an anhydrous citric acid; the drug stock solution comprises a mass-to-volume ratio of the RAPA to the drug solvent of 0.1 to 60 mg/ml;
   the drug solvent comprises absolute ethanol and a latent solvent, the latent solvent is one or more selected from the group consisting of propylene glycol (PG), polyethylene glycol (PEG) 300, and PEG 400; the absolute ethanol in the drug solvent has a volume percentage of 1% to 50% and the latent solvent in the drug solvent has a volume percentage of 50% to 99%;
   the surfactant in the diluent has a volume percentage of 0.5% to 50%, and the surfactant is PEG-15 hydroxystearate.

2. The RAPA self-microemulsifying injection according to claim 1, wherein the antioxidant is one or more selected from the group consisting of 2,6-tert-butyl-4-methylphenol, bis (3,5-tert-butyl-4-hydroxyphenyl) sulfide, tetrakis [β-(3,5-tert-butyl-4-hydroxyphenyl) propionic acid], pentaerythritol oleate, butylated hydroxytoluene (BHT), α-tocopherol, thioglycerin, and butylated hydroxyanisole (BHA).

3. The RAPA self-microemulsifying injection according to claim 1, wherein the diluent further comprises a metal chelating agent.

4. The RAPA self-microemulsifying injection according to claim 3, wherein the metal chelating agent is one or more selected from the group consisting of ethylenediamine tetraacetic acid (EDTA), nitrilotriacetic acid (NTA), diethylenetriaminepentaacetic acid (DTPA), a salt of the DTPA, citric acid, tartaric acid, gluconic acid, hydroxyethylethylenediaminetriacetic acid (HEDTA), polyacrylic acid (PAA), polymethylacrylic acid (PMAA), hydrolyzed polymaleic anhydride (HPMA), fumaric acid-propenesulfonic acid copolymer, dihydroxyethylglycine, and calcium disodium edetate.

5. A preparation method of the RAPA self-microemulsifying injection according to claim 1, comprising:
   (1) thoroughly mixing the absolute ethanol and the latent solvent to obtain a mixed solution, adding the RAPA to the mixed solution, and then adding the antioxidant and the anhydrous citric acid to obtain the drug stock solution;
   (2) thoroughly mixing the surfactant, the water, and a metal chelating agent to obtain the diluent; and
   (3) diluting the drug stock solution with the diluent to a desired concentration to obtain the RAPA self-microemulsifying injection for use.

6. The preparation method according to claim 5, wherein the antioxidant is one or more selected from the group consisting of 2,6-tert-butyl-4-methylphenol, bis (3,5-tert-butyl-4-hydroxyphenyl) sulfide, tetrakis [β-(3,5-tert-butyl-4-hydroxyphenyl) propionacid], pentaerythritol oleate, butylated hydroxytoluene (BHT), α-tocopherol, thioglycerin, and butylated hydroxyanisole (BHA).

7. The preparation method according to claim 5, wherein the metal chelating agent is one or more selected from the group consisting of ethylenediamine tetraacetic acid (EDTA), nitrilotriacetic acid (NTA), diethylenetriaminepentaacetic acid (DTPA), a salt of the DTPA, citric acid, tartaric acid, gluconic acid, hydroxyethylethylenediaminetriacetic acid (HEDTA), polyacrylic acid (PAA), polymethylacrylic acid (PMAA), hydrolyzed polymaleic anhydride (HPMA), fumaric acid-propenesulfonic acid copolymer, dihydroxyethylglycine, and calcium disodium edetate.

* * * * *